(12) United States Patent
Cicalis

(10) Patent No.: US 10,864,349 B2
(45) Date of Patent: Dec. 15, 2020

(54) SYSTEM AND METHOD FOR PACKAGING AN ELONGATE MEDICAL DEVICE

(71) Applicant: Perry Cicalis, Bridgewater, MA (US)

(72) Inventor: Perry Cicalis, Bridgewater, MA (US)

(73) Assignee: ARGOS CORPORATION, Taunton, MA (US)

( * ) Notice: Subject to any disclaimer, the term of this patent is extended or adjusted under 35 U.S.C. 154(b) by 62 days.

(21) Appl. No.: 15/881,901

(22) Filed: Jan. 29, 2018

(65) Prior Publication Data

US 2018/0214665 A1 Aug. 2, 2018

Related U.S. Application Data

(60) Provisional application No. 62/453,714, filed on Feb. 2, 2017.

(51) Int. Cl.
| | |
|---|---|
| *B29C 48/00* | (2019.01) |
| *A61M 25/00* | (2006.01) |
| *B32B 1/08* | (2006.01) |
| *B32B 27/08* | (2006.01) |
| *B32B 27/32* | (2006.01) |
| *B32B 27/40* | (2006.01) |
| *B29C 48/10* | (2019.01) |
| *B29C 48/21* | (2019.01) |
| *B29C 48/151* | (2019.01) |
| *B29L 31/00* | (2006.01) |

(Continued)

(52) U.S. Cl.
CPC ....... *A61M 25/002* (2013.01); *B29C 48/0021* (2019.02); *B29C 48/10* (2019.02); *B29C 48/151* (2019.02); *B29C 48/21* (2019.02); *B32B 1/08* (2013.01); *B32B 27/08* (2013.01); *B32B 27/32* (2013.01); *B32B 27/40* (2013.01); *A61M 2207/00* (2013.01); *B29K 2023/065* (2013.01); *B29K 2075/00* (2013.01); *B29L 2031/7542* (2013.01); *B32B 2307/536* (2013.01); *B32B 2535/00* (2013.01)

(58) Field of Classification Search
CPC ...... A61M 25/002; A61B 50/30; B32B 27/40; B29C 48/0021
See application file for complete search history.

(56) References Cited

U.S. PATENT DOCUMENTS

| | | | |
|---|---|---|---|
| 4,583,641 A | 4/1986 | Gelzer | |
| 5,344,011 A * | 9/1994 | DiBernardo | A61M 25/002 206/364 |

(Continued)

OTHER PUBLICATIONS

International Search Report dated Aug. 24, 2018 from the corresponding PCT Patent Application No. PCT/US2018/032520.

*Primary Examiner* — Scott W Dodds
(74) *Attorney, Agent, or Firm* — Grogan, Tuccillo & Vanderleeden, LLP

(57) ABSTRACT

A method of manufacturing a clipless package for an elongate medical device or other elongate device is provided. The subject invention utilizes adhesives and material surface characteristic modification to bond the tube surfaces together, which overcomes the deficiencies of currently utilized packaging methods. The bonds can be created by a singular application of adhesive or in plurality or combination with a surface modifier, coated surface and/or a surface treatment, or by selection of a singular polymer outer layer that is tacky when fully cooled, whose morphology changes post-extrusion.

13 Claims, 8 Drawing Sheets

(51) Int. Cl.
    *B29K 75/00*    (2006.01)
    *B29K 23/00*    (2006.01)

(56)            References Cited

U.S. PATENT DOCUMENTS

| | | | |
|---|---|---|---|
| 5,525,178 | A | 6/1996 | Roggenbuck |
| 5,928,744 | A * | 7/1999 | Heilmann ............... A61L 29/14 |
| | | | 428/36.6 |
| 6,102,039 | A * | 8/2000 | Springett ................. B32B 5/26 |
| | | | 128/206.12 |
| 6,299,596 | B1 * | 10/2001 | Ding ....................... A61L 29/12 |
| | | | 604/96.01 |
| 7,549,270 | B2 | 6/2009 | Rowe et al. |
| 2003/0075459 | A1 | 4/2003 | Allgood et al. |
| 2004/0055919 | A1 * | 3/2004 | Rowe .................. A61M 25/002 |
| | | | 206/438 |
| 2005/0131445 | A1 * | 6/2005 | Holman ............ A61M 25/0069 |
| | | | 606/194 |
| 2005/0170122 | A1 * | 8/2005 | Fahrenholz ............... B32B 1/08 |
| | | | 428/36.91 |
| 2007/0151889 | A1 | 7/2007 | Brady |
| 2008/0113083 | A1 | 5/2008 | Sutermeister et al. |
| 2012/0220897 | A1 * | 8/2012 | Taylor ................ A61M 25/002 |
| | | | 600/585 |
| 2012/0261290 | A1 * | 10/2012 | Limjaroen .......... A61M 25/002 |
| | | | 206/364 |
| 2015/0330539 | A1 * | 11/2015 | Simonsohn ............. B29C 48/30 |
| | | | 138/154 |

\* cited by examiner

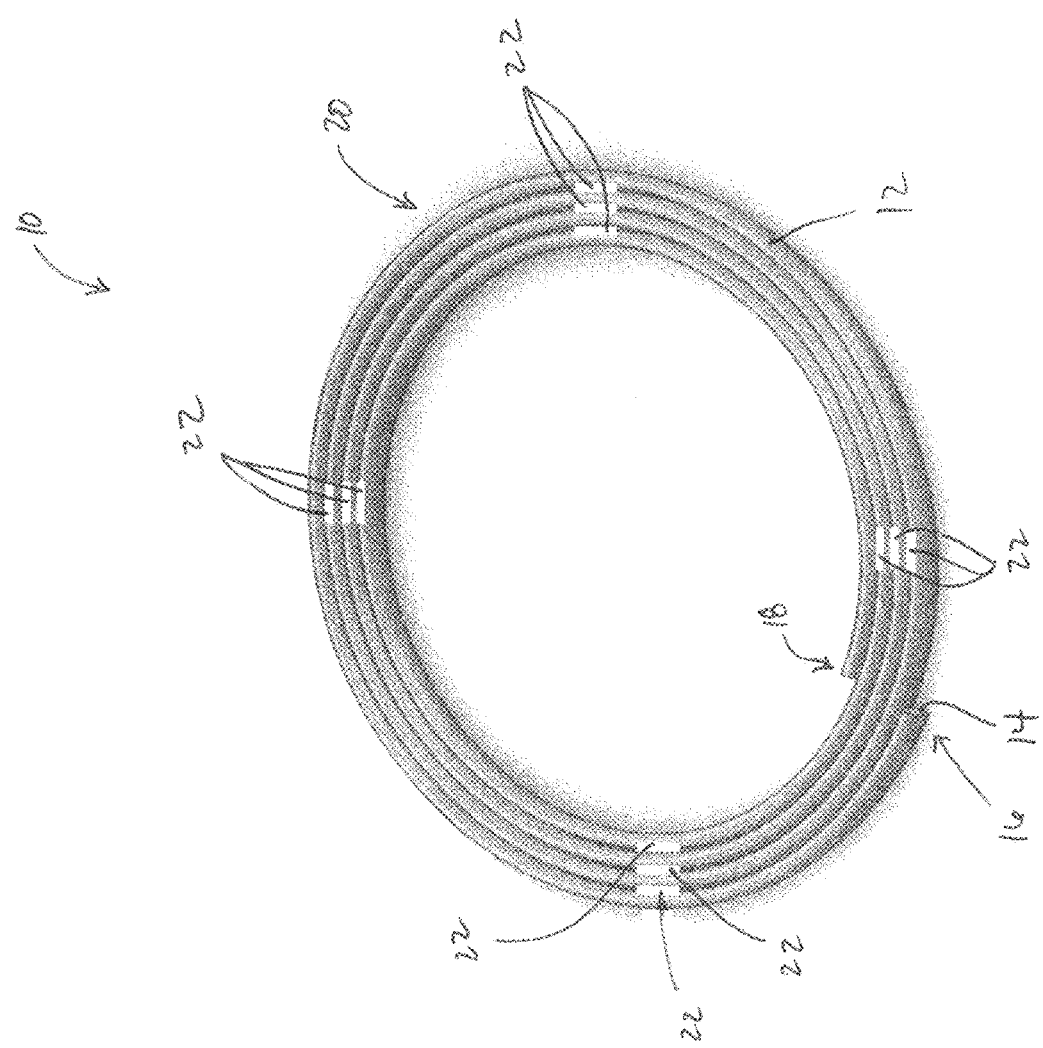

SYSTEM AND METHOD FOR PACKAGING AN ELONGATE MEDICAL DEVICE

CROSS-REFERENCE TO RELATED APPLICATIONS

This application claims the benefit of U.S. Provisional Application Ser. No. 62/453,714, filed on Feb. 2, 2017, which is hereby incorporated by reference herein in its entirety.

FIELD OF THE INVENTION

The present invention relates generally to packaging for medical devices and, more particularly, to a method of manufacturing packaging for elongate medical devices such as catheters and guide wires.

BACKGROUND OF THE INVENTION

Various elongate medical devices exist which are designed to navigate narrow passages within the human body. Examples of such devices include catheters and guide wires. These devices are typically long, narrow (having a high length to diameter ratio) and flexible, which give rise to a variety of packaging challenges. One form of packaging for such elongate devices which is particularly common includes a coiled tube having a lumen into which the elongate medical device can be loaded without kinking or distorting the device.

As is known in the art, existing packaging can contain multiple coiled tubes in various configurations to accommodate a variety of elongated devices in a single package. Typically, the coiled tubes are manufactured from thermoplastic polymers, such as polyolefin materials, which are low cost. Two of the most common polyolefins utilized include polyethylene and polypropylene. Polyolefins can be thermoplastic or thermosetting and refer to a family of polymers that are formed from an alkene (CnH2n) group. The nature of polyolefins is that they have low cost, high purity, low surface energy, are easily sterilized and are easily manufactured through extrusion, a common plastic manufacturing process.

Formation of coiled tube packages has proven difficult, however, as the individual coils have a natural tendency to separate from one another. In an effort to maintain the coiled configuration of the tube, various mechanical clips have been designed to individually engage the coils and hold them in close proximity. By maintaining each of the coils in a fixed relationship with a clip, the coiled configuration of the tube can be loosely maintained. After the coiled tube has been formed and the elongate device has been loaded into the tube, the device and tube are enclosed in a pouch and sealed for sterilization and ultimate distribution of the product.

The use of clips to hold the coils together, however, has been problematic. In particular, clips can puncture the pouch within which the coil and device are enclosed during shipping or handling, compromising sterility and rendering the elongate device unusable. In addition, the use of clips increases manufacturing costs and time. Moreover, in certain situations the tubes may still come loose from the clips, necessitating re-clipping.

Efforts to address the drawbacks associated with the use of mechanical clips have heretofore focused on thermal bonding of the coils to maintain the coiled nature of the packaging. Thermal bonding involves heating a portion of the tube sufficiently to melt the surface of adjacent tube coils, which creates an interface of melted polymer that when cooled is essentially a singular area of material or a weld of the thermoplastic tube material. While thermal bonding substantially eliminates the issue of pouch puncture, it can be more costly due to manufacturing time as well as other problems that can arise melting and reforming of the weld area. An inherent problem with thermal bonding is that care must taken to ensure that the inside diameter (lumen) of the tubes are not occluded due to the heating process. Indeed, as tube walls are made thinner, there is a higher likelihood of breaching the lumen or creating an area that could be breached with strain or impact on the package. Moreover, thermal bonding or welding also restricts the minimum thickness of the tube wall that can be utilized, which minimizes any potential material cost savings. Thermal bonding can also cause damage to the medical device contained within the coil due to an occlusion in welding caused by the process heat. These costly medical devices, if damaged, can put patients at risk and add cost to the supply chain.

In view of the above, there is a need for a packaging, and method of manufacturing packaging, for elongate medical devices and other elongate devices that is less costly and less prone to defects and other undesirable effects than packaging and methods currently utilized.

SUMMARY OF THE INVENTION

It is an object of the present invention to provide a method of manufacturing packaging for an elongate medical device.

It is another object of the present invention to provide a method of manufacturing packaging for an elongate medical device that is less costly than existing methods.

It is another object of the present invention to provide a method of manufacturing packaging for an elongate medical device that is less prone to defects in the coils, such as occlusions.

It is another object of the present invention to provide a method of manufacturing packaging for an elongate medical device that facilitates the use of thin-walled coils.

It is another object of the present invention to provide a package for an elongate medical or surgical device.

These and other objects are achieved by the present invention.

According to one embodiment of the present invention, a method for creating a clipless package for an elongate medical device or other elongate device is provided. The subject invention utilizes adhesives and material surface characteristic modification to bond the tube surfaces together, which overcomes the deficiencies of currently utilized packaging methods. The bonds can be created by a singular application of adhesive or in plurality or combination with a surface modifier, coated surface and/or a surface treatment.

According to an embodiment of the present invention, a method of manufacturing a package for an elongate device is provided. The method includes providing a tube having a lumen extending through at least a portion of the tube, arranging the tube into a coiled configuration such that turns of the tube are placed in adjacent, spiral relationship, and non-thermally bonding at least a first turn of the tube to a second turn of the tube to maintain the coiled configuration of the tube.

According to another embodiment of the present invention, a package for an elongate device is provided. The package includes an elongate tube having a plurality of turns defining a spiral coil configuration of the tube, and a plurality of adhesive bonds between adjacent turns of the tube, the adhesive bonds maintaining the spiral coil configuration of the tube.

According to yet another embodiment of the invention, a method of manufacturing a package for an elongate medical device is provided. The method includes forming a tube having a lumen extending through at least a portion of the tube, modifying a surface of the tube to facilitate adhesion of adjacent turns of the tube to one another using an adhesive, arranging the tube into a spiral coil configuration, and bonding at least one turn of the tube to an adjacent turn of the tube using an adhesive to maintain the spiral coil configuration.

BRIEF DESCRIPTION OF THE DRAWINGS

The present invention will be better understood from reading the following description of non-limiting embodiments, with reference to the attached drawings, wherein below:

FIG. 4 is an enlarged, detail view of the end of a tube of the package, showing a surface modification that enhances adhesive bonding.

DETAILED DESCRIPTION OF THE PREFERRED EMBODIMENT

Figure 1:
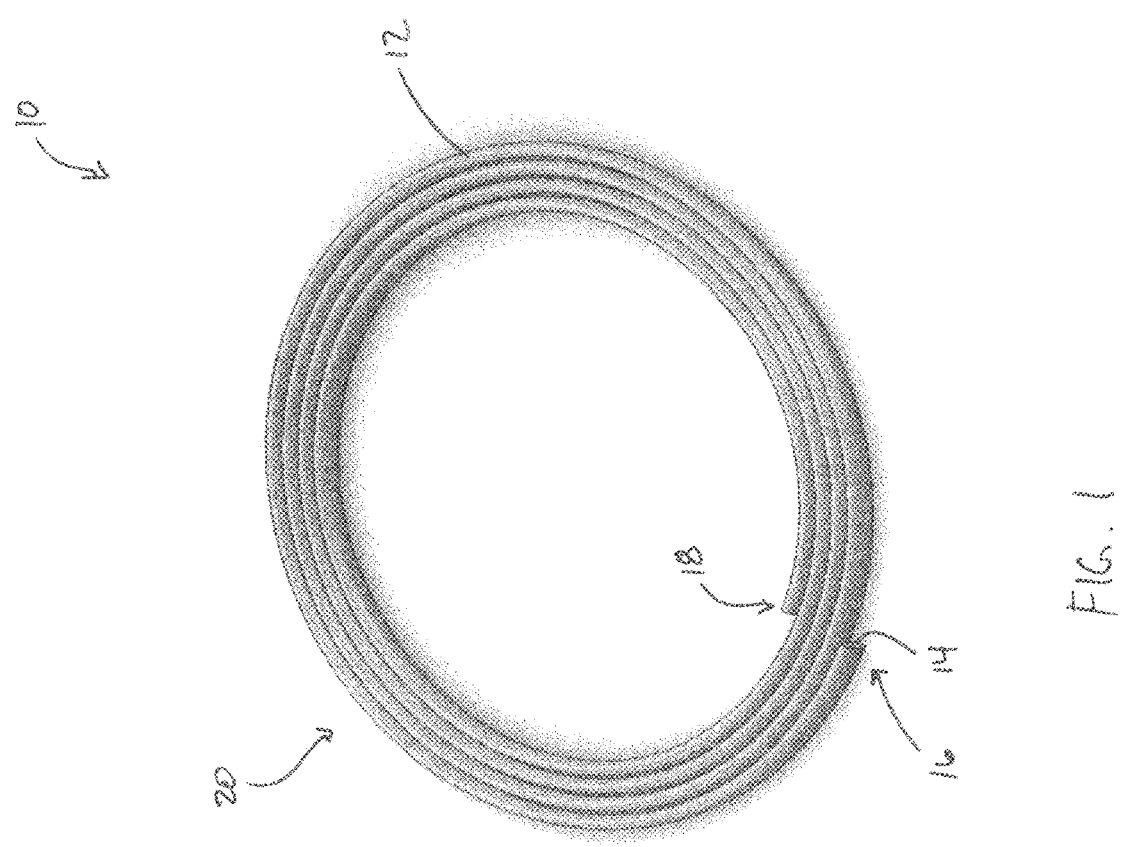
FIG. 1 is a perspective view of a package for an elongate medical device, according to an embodiment of the present invention.
Figure 2:
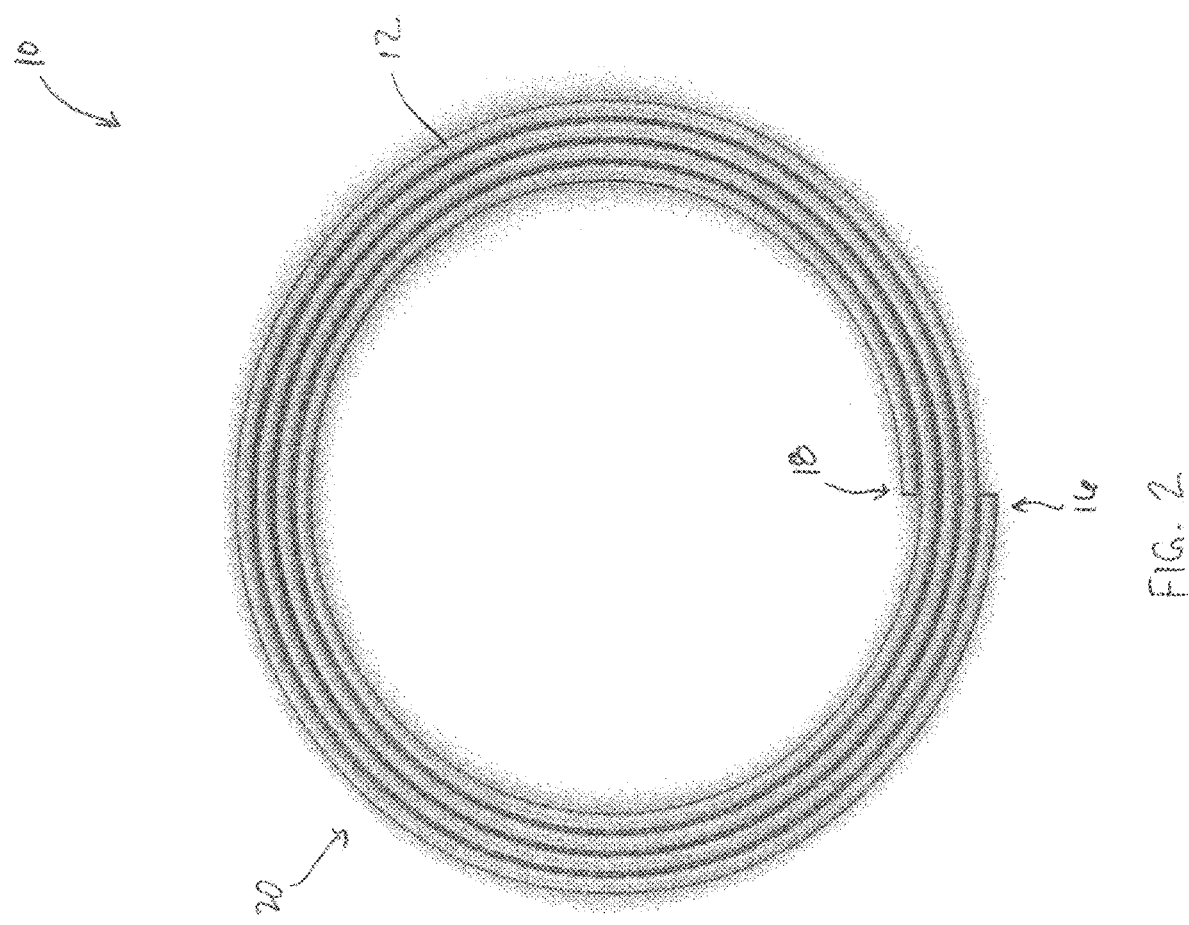
FIG. 2 is a top plan view of the package of FIG. 1.
Figure 3:
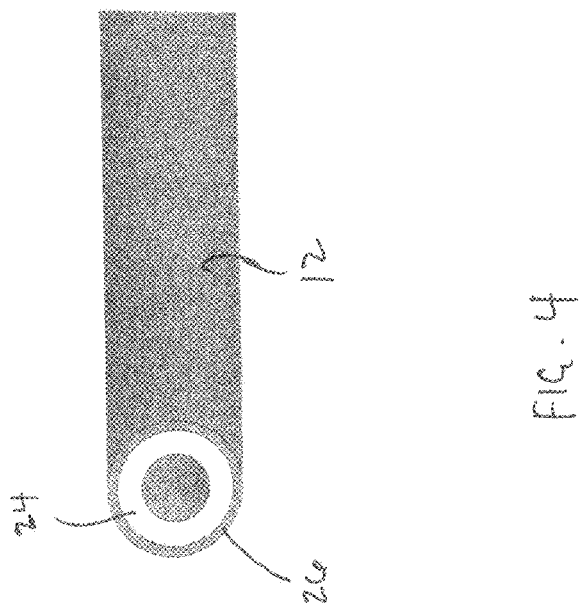
FIG. 3 is a perspective view of the package of FIG. 1, illustrating adhesive bonding locations.

Referring to FIGS. 1-3, a package 10 for en elongate device, such as an elongate medical device, is illustrated. Although the package 10 is specifically adapted to retain, transport, distribute, and deliver a catheter or guide wire (not shown), the package 10 can be adapted for use with any flexible elongate medical instrument or device, or any elongate device, more generally, without departing from the broader aspects of the present invention.

As shown therein, the package 10 includes at least one tube 12 having a lumen 14 that extends between opposing ends 16 and 18. The tube 12 may be formed by extrusion or other means known in the art, and is wound into a coil 20. While FIGS. 1-3 illustrate tube 12 formed into a circular coil, other coil configurations such as elliptical and the like are also possible without departing from the broader aspects of the invention. Preferred tube materials include materials that have high "slip" or allow the elongated device to slide readily through the tube 12. For example, polyolefins such as polyethylene and polypropylene, as well as many other polymers, may be utilized. Other materials may also be utilized without departing from the broader aspects of the invention.

As best illustrated in FIG. 3, as the tube 12 is wound into a coil, the turns of the tube 12 may be brought into adjacent, spiral relationship. Adhesive 22 is then used between the adjacent turns of the tube 12 to maintain the coiled configuration. In this manner, the present invention uses adhesive and material technology to create a non-thermally bonded, clipless package for elongated surgical and other devices. In particular, as shown in FIG. 3, in an embodiment, the extruded tube 12 is coiled and adhesively bonded at various points between adjacent turns of the tube 12 to permanently affix the turns to one another to maintain the coiled shape. That is, the tube 12 consists of adhesive points 22 tacked along the circumference of the coil at multiple points (at spaced radial locations) to allow for flexibility within the coil. Importantly, by tacking the turns of the tube to one another via the arrangement shown in FIG. 3, when a force is applied to the tacked coil the coil can take up the force by separating in the areas that are not physically tacked.

In an embodiment, the turns of the tube 12 may be tacked to one another every 90 degrees (i.e., at four radial locations of the package). In another embodiment, the turns of the tube may be tacked to one another every 180 degrees (i.e., at two radial locations of the package). Other adhesive bonding configurations may also be used to provide a desired level of rigidity or flexibility.

In another embodiment, rather than adhesively bonding the adjacent turns at spaced radial locations, the tube 12 can be continuously bonded along the entirety of adjacent turns. In such an embodiment, the adhesive 22 is a low durometer adhesive that is flexible itself and is bonded completely around the circumference of the turns with no gaps. The flexible adhesive flexes with the bonded tubular package 10 when a force is applied, and flexes along with the turns of the tube 12 without any separation of the turns. Both embodiments contemplated herein provide a means to absorb impact that may be caused by handling, while still protecting the elongate device held inside. Specific configurations are dependent on package needs, and can include adhesive bonding of bridge material between the adjacent coils as well, as disused in detail hereinafter.

In an embodiment, the low durometer adhesive may be an adhesive offered under the name Loctite® AA 3108 (a 72 on the Shore A scale, and listed as an acrylated urethane acrylic liquid adhesive). Elongation after cure is listed at 330% and Tensile Modulus is 2670 psi. The properties of this low durometer flexible adhesive allow for the bond to act as a shock absorber to the more rigid tubing. The combination of these properties can be varied to enhance the final package properties. The coil can be made to be rigid and non-moving with a hard durometer inflexible adhesive or made to bend and flex between coils in the package form with a low durometer flexible adhesive. Other low durometer adhesives may include, for example, Loctite® 4307, Loctite® AA3108, Loctite® 3311, Loctite® 4310, Loctite® 3201, and Loctite® 3105.

While the tube 12 is preferably manufactured from a high "slip" material, the low surface energy of the material and lack of reactive sites on the tube surface required for adhesive bonding to be effective requires special considerations and treatment. In order to create a substantive bond that will work for the packaging 10, the surface chemistry or surface energy of the polymer tube 12 is chosen carefully or modified to be of sufficient surface energy to readily allow for adhesive bonding utilizing the adhesive 22. As discussed hereinafter, the present invention contemplates a number of processes that can be utilized to modify the surface chemistry or surface energy of the tube 12 to facilitate adhesive bonding. For example, in an embodiment, the surface of the tube 12 may be modified utilizing at least one of corona, flame or plasma treatment. In yet other embodiments, primers can also be applied to the exterior surface of the tube 12 at the adhesive bonding locations that will temporarily change the surface energy of the product to allow for adhesion. Examples of primers that may be used include Loctite® primer SF 7701 (a medical grade primer used to enhance the surface energy of polyolefin materials to increase bond strength with cyanoacrylate adhesives), Loctite® SF 770, and MasterBond x-18 primer.

The nature of polyolefins, however, is that they have high chemical resistance, which also adds complexity to the art of surface modification when selecting a primer. The present invention therefore envisions that surface modification of the tube 12 can also be made through the use of additives to the polymer. Modifiers may include any additive that increases the reactivity of the polymer surface, in order to allow for chemical bonding utilizing the adhesive 22. In an embodiment, a silane-based coupling agent may be used as an additive to the base polymer to enhance surface reactivity of the tube 12.

Applying a coating to the tube is yet another method that will result in a modified surface chemistry that facilitates adhesive bonding. In an embodiment, a coating can be applied to the tube 12 through processes such as, for example, coextrusion, tandem extrusion, fluidized bed and spray coating. The selection of method and the selection of a coating material is dependent upon the composition of the tube 12 as well as the adhesive 22. Extruded coatings, known as "tie layers", are typically used in a melt state and require heat to activate the reactive groups to the extent that dissimilar materials can be bonded. These coatings, when added to the tube extrusion process, allow for increased bond strength of adhesives between adjacent coils of the tube 12 because they change the surface energy and or leave a greater number of reactive groups available to bond to the adhesive 22.

As indicated above, the choice of adhesive is dependent on the material of the tube 12, the needs of manufacturing, and material bond strength for the application. In one preferred embodiment, the adhesive 22 is a UV curable adhesive, and the tube 12 is a co-extruded tube having an inner wall 24 of polyethylene and a thin anhydride modified polyethylene outer layer 26 (see FIG. 4). The co-extruded tube is formed into a coiled configuration, as illustrated in FIGS. 1-3. The outer tube layers 26 are adhesive bonded between adjacent coils at the tube surfaces which are now more reactive due to the outer layer material 26. The UV curable adhesive 22 is a fast acting photo initiated cyanoacrylate flash cure adhesive product. The wavelength and the intensity of the ultraviolet light were found to affect the bond time and strength. The bond strength is significantly greater than a standard polyethylene to polyethylene bond and is enhanced further when a primer is used prior to the adhesive application. These materials are available as both FDA and USP Class VI materials, including the adhesive and primer. The durometer of the adhesive selected in this embodiment is essential in its successful application.

Figure 5:
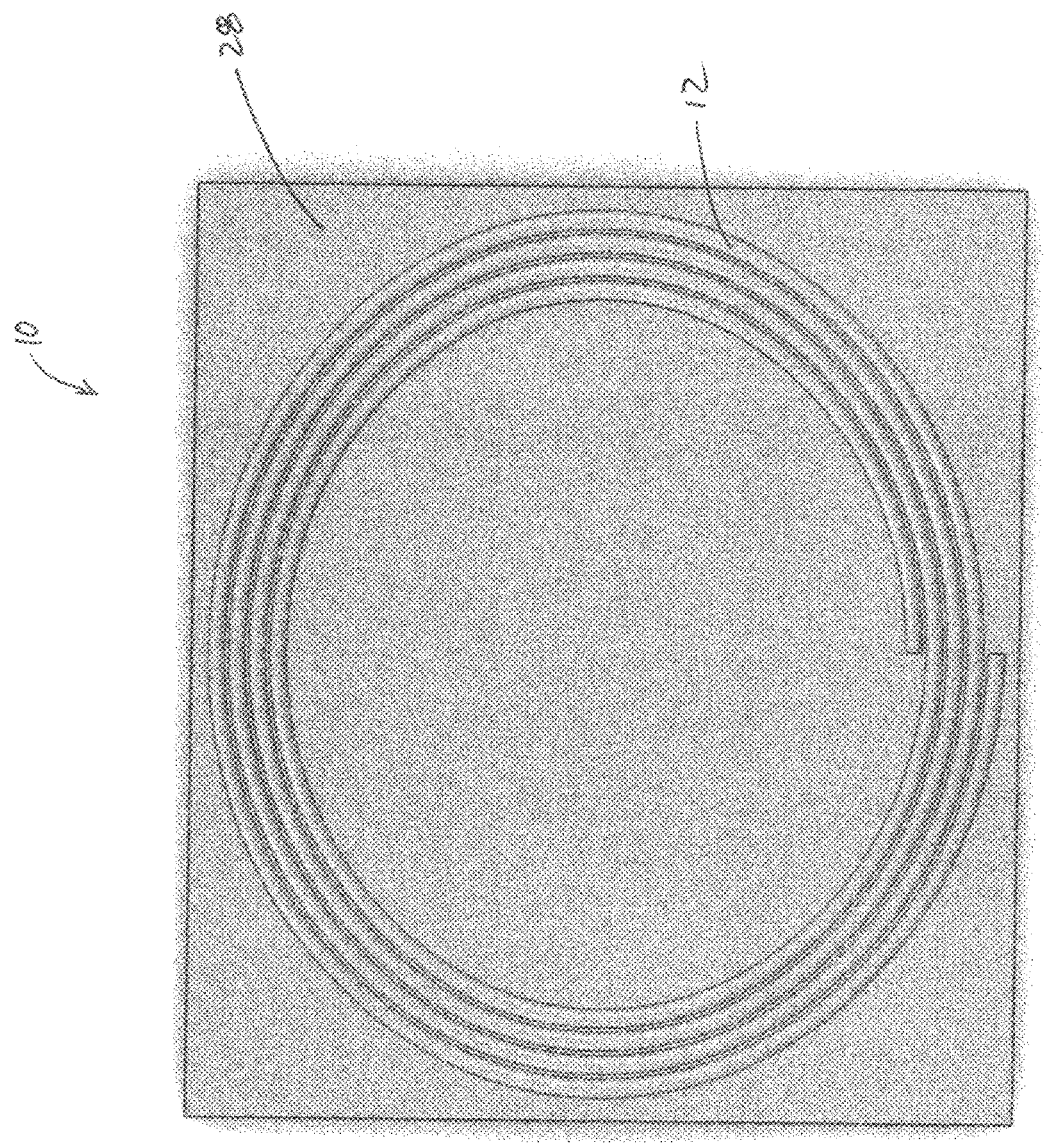
FIG. 5 is a top plan view of the package of FIG. 1, shown affixed to a backing layer.

Turning now to FIG. 5, in an embodiment, the coil 20 may be attached to a backing card 28. The coil 20, in addition to one or more retention accessories (not shown) may be attached to the backing card 28 using the adhesive. Standard anchoring methods can be applied as well. This preferred embodiment can be made with various coextruded adhesive layers and a commonly used inner layer material such as high density polyethylene. The outer layer can be a polyolefin which has a grafted reactive group attached to the polymer backbone. While this is one preferred embodiment of selected materials, the use of other outer layer materials such as a material known as Kraton by its trade name offer the ability to create the package with alternate inner layer materials and adhesive solutions to create the elongated surgical device package.

Other materials that enhance the ability to adhesive bond polyolefins and low surface energy materials used in the manufacture of elongated surgical device packaging, whether currently known or to be developed, would not alter the intent of the present invention to more readily allow adhesive bonding of the adjacent coils of a tube into a clipless elongated surgical device package for high L/D surgical devices.

The application of a thermoplastic elastomer, namely, a polyether block amide (PEBA) such as, for example, Arkema Pebax grades in a co-extrusion with HDPE is another embodiment of the invention. The thin, coextruded outer layer of Pebax is bonded at various points along the coil with a flash cure UV curable adhesive to form the tube into the coiled package. No primers or additional modifiers are needed in this embodiment to obtain bond strength and package integrity greater than needed in final application.

Figure 6:
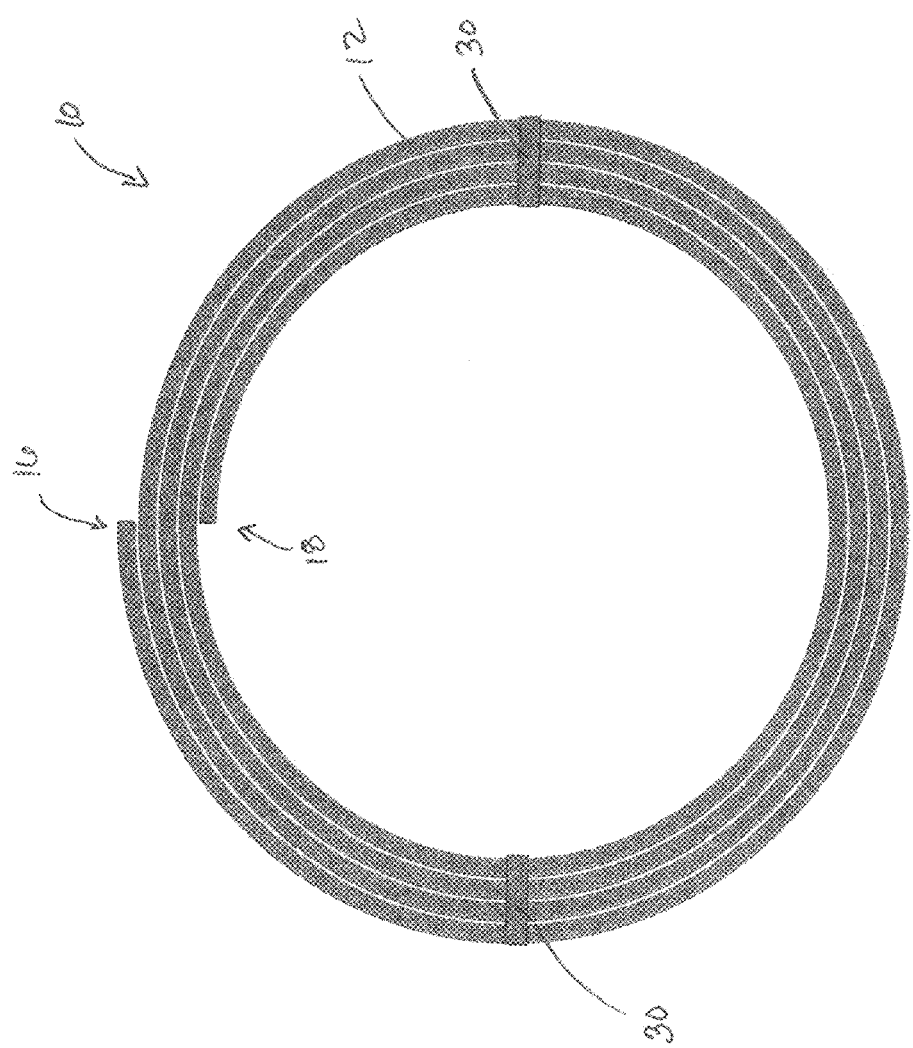
FIG. 6 is a top plan view of a package for an elongate medical device, according to another embodiment of the present invention.

Turning now to FIG. 6, in an embodiment, braces 30 may be bonded across the turns of the tube 12 of the spiral coil utilizing an adhesive. The braces 30 may be utilized in place of, or in addition to, the adhesive bonding between the turns of the tube 12. In an embodiment, the braces 30 are made of a material that is easily bonded along its length and is of sufficient strength to keep the coils separate.

Figure 7:
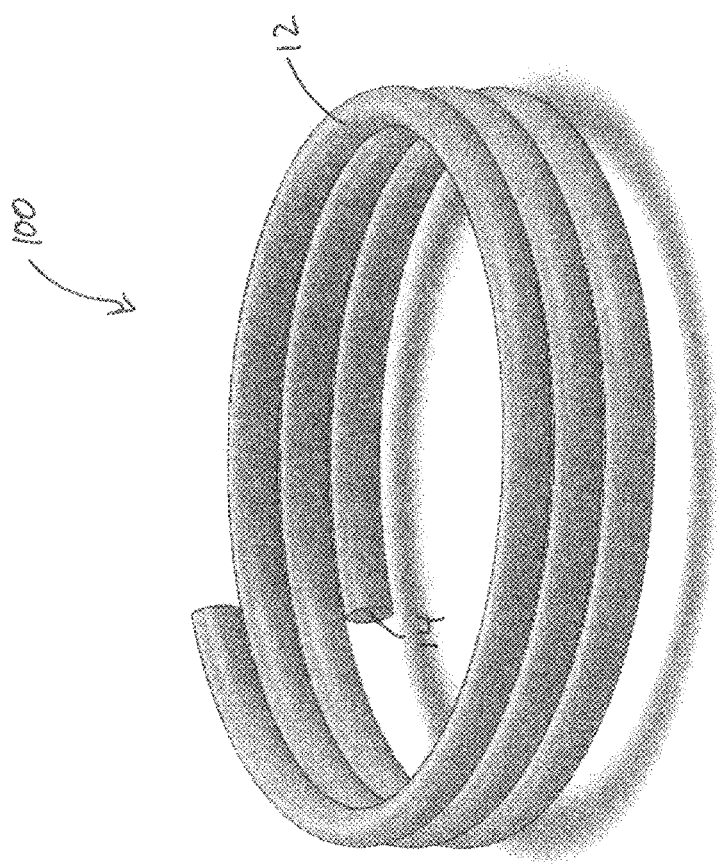
FIG. 7 is a perspective view of a package for an elongate medical device, according to another embodiment of the present invention.
Figure 8:
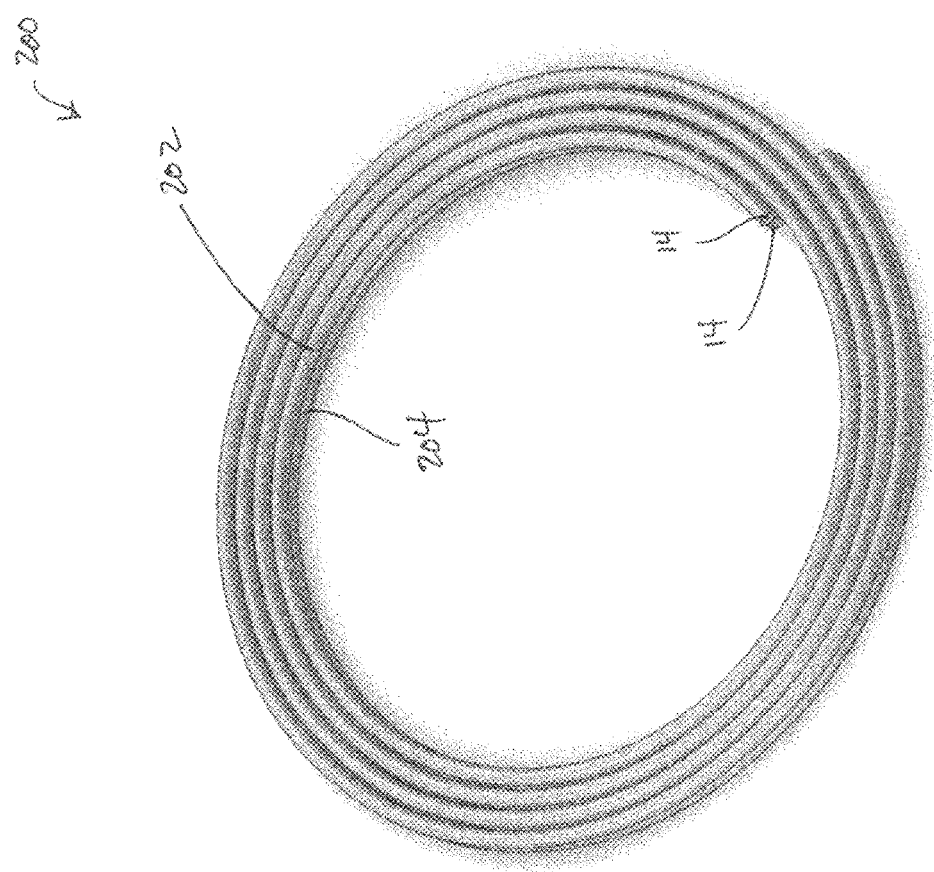
FIG. 8 is a perspective view of a package for an elongate medical device, according to yet another embodiment of the present invention.

Turning now to FIG. 7, in other embodiments the coiled package can be configured in a stacked coil 100 (in which the turns are stacked on one another vertically) rather than the spiral coil version of FIGS. 1-6 (in which the turns are positioned horizontally with respect to one another). In this embodiment, the adhesive is applied between the vertically adjacent turns of the tube. In yet another embodiment, as illustrated in FIG. 8, the coiled package 200 can include more than one tube (e.g., tubes 202, 204) with more than one diameter, to allow for packaging of more than one elongated device such as a guide wire and catheter.

As discussed above, the present invention contemplates the non-thermal bonding of polymer tubing through the use of adhesives and surface modification such as, for example, coextrusion, compounding or blending of additives or other polymers to the monolayer or multi-layered tube construction. Coupling agents can also be used to modify the chemistry of the polymer tube substrate to enhance the surface characteristics of polyolefins and other polymers to more readily bond utilizing adhesives. The present invention therefore obviates the need to use mechanical clips to hold the coil together, and provides a functionally improved package and more efficient alternative to thermal bonding.

In certain embodiments, other layers may be applied to the interior of the tube and/or additives may be added to the base polymer to provide a near frictionless inner surface. This facilitates the insertion and removal of delicate or fragile surgical or medical devices, thereby reducing the likelihood of damage during such insertion or removal. The increase 'slip' on the inner surface of the tube can also provide for faster insertion of the medical device into the package, thereby increasing product throughput.

Additionally, another embodiment allows greater bonding integrity of end caps due to the enhancements and techniques described herein. For example, polyolefin or other polymer end caps can attached to the elongated package in a manner similar to how the turns of the tube are bonded to one another, as described above.

An additional embodiment uses the properties of Thermoplastic Polyurethane (TPU), for example, as an outer layer in a co-extrusion. The morphology of the TPU grade that is utilized allows the packaging tube to be coiled and bonded as it is collected. This embodiment allows for a coiling operation as the cooled extruded tubes are collected in an extrusion operation. Bonding is created by intimate contact at points between the outside of the tube surface and attaching it to itself along its length, thus bonding the material after it is cooled in the extrusion process. The chemical nature of the TPU's hard and soft segments create a tacky product immediately as extruded (even though it is fully cooled), which mitigates over time (less than 24 hours with many grades) to a non-tacky smooth surface. The points of the tube that were placed in contact with each other post extrusion are therefore fully bonded, with no application of heat.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A method of manufacturing a package for an elongate device, comprising the steps of:
    forming a tube having a lumen extending through at least a portion of the tube, via an extrusion process, wherein the extruded tube has a tacky exterior surface;
    arranging the tube into a coiled configuration such that turns of the tube are placed in adjacent, spiral relationship; and
    contacting the tacky exterior surface of a first turn of the tube to a second turn of the tube to bond the first turn of the tube to the second turn of the tube, without applying heat or an adhesive, to maintain the coiled configuration of at least the first turn and the second turn of the tube.

2. The method according to claim 1, wherein:
    the extrusion process is a coextrusion process; and
    the step of forming the tube includes forming a Thermoplastic Polyurethane outer layer with the tube.

3. The method according to claim 2, wherein:
    the step of contacting the first turn of the tube to the second turn of the tube occurs while an outer surface of the tube is tacky after the coextrusion process.

4. The method according to claim 1, further comprising the step of:
    cooling the tube;
    wherein the step of contacting the first turn of the tube to the second turn of the tube is carried out after the tube is cooled.

5. The method according to claim 1, further comprising the step of:
    fully cooling the tube;
    wherein the step of contacting the first turn of the tube to the second turn of the tube is carried out after the tube is fully cooled.

6. The method according to claim 1, wherein:
    the step of contacting the tacky exterior surface of the first turn of the tube to the second turn of the tube to bond the first turn of the tube to the second turn of the tube includes only contacting discrete points along the exterior surface of the first turn of the tube to discrete points along the second turn of the tube such that the tube is not continuously bonded along its entire length.

7. A method of manufacturing a package for an elongate device, comprising the steps of:
    forming a tube having an inner layer and an outer layer, the inner layer defining a lumen extending through at least a portion of the tube, the outer layer being formed from a Thermoplastic Polyurethane;
    wherein forming the outer layer occurs via an extrusion process and provides the outer layer with a tacky exterior surface;
    arranging the tube into a coiled configuration such that turns of the tube are placed in adjacent, spiral relationship; and
    contacting a portion of the tacky exterior surface along the first turn of the tube to a portion of the outer layer along the second turn of the tube to bond the first turn of the tube to the second turn of the tube, without applying heat or an adhesive, to maintain the coiled configuration of at least the first turn and the second turn of the tube.

8. The method according to claim 7, wherein:
    the step of forming the tube having the inner layer and the outer layer is carried out via coextrusion.

9. The method according to claim 7, further comprising the step of:
    cooling the tube;
    wherein the step of contacting the portion of the outer layer along the first turn to the portion of the outer layer along the second turn is carried out after the tube is cooled.

10. The method according to claim 7, further comprising the step of:
    fully cooling the tube;
    wherein the step of contacting the portion of the outer layer along the first turn to the portion of the outer layer along the second turn is carried out after the tube is fully cooled.

11. A method of manufacturing a package for an elongate device, comprising the steps of:
    extruding a Thermoplastic Polyurethane material to form a tube having a lumen extending through at least a portion of the tube;
    cooling the tube;
    while an outer surface of the tube remains tacky following the extruding, and after cooling the tube, arranging the tube into a coiled configuration such that turns of the tube are placed in adjacent, spiral relationship; and
    contacting adjacent turns of the tube to one another to non-thermally and non-adhesively bond the adjacent turns to one another via the tacky outer surface, to maintain the coiled configuration of at least the first turn and the second turn of the tube.

12. The method according to claim 11, wherein:
    the tube is arranged into the coiled configuration, and the adjacent turns of the tube are contacted with one another, as the tube is collected from an extrusion device such that steps of extruding the Thermoplastic Polyurethane material to form the tube, arranging the tube into the coiled configuration and contacting the adjacent turns of the tube to one another are carried out in a single inline process.

13. The method according to claim 12, wherein:
extruding the Thermoplastic Polyurethane material to form a tube includes coextruding the tube.

\* \* \* \* \*